US010507274B2

(12) United States Patent
Wallinger et al.

(10) Patent No.: US 10,507,274 B2
(45) Date of Patent: Dec. 17, 2019

(54) FLOW THROUGH HEATER

(71) Applicant: WATLOW ELECTRIC MANUFACTURING COMPANY, St. Louis, MO (US)

(72) Inventors: Martin Wallinger, Golling (AT); Gernot Antosch, Golling (AT); Reiner Lehnert, Ubstadt-Weiher (DE); Wolfgang Pöschl, Golling (AT); Gerhard Schefbänke, Golling (AT)

(73) Assignee: Watlow Electric Manufacturing Company, St. Louis, MO (US)

( * ) Notice: Subject to any disclaimer, the term of this patent is extended or adjusted under 35 U.S.C. 154(b) by 563 days.

(21) Appl. No.: 15/339,112

(22) Filed: Oct. 31, 2016

(65) Prior Publication Data

US 2017/0065758 A1 Mar. 9, 2017

Related U.S. Application Data

(63) Continuation of application No. 13/096,993, filed on Apr. 28, 2011, now Pat. No. 9,532,404.

(Continued)

(51) Int. Cl.
*H05B 3/40* (2006.01)
*H05B 3/48* (2006.01)
(Continued)

(52) U.S. Cl.
CPC ............ *A61M 1/1629* (2014.02); *A61M 5/44* (2013.01); *H05B 3/40* (2013.01); *H05B 3/58* (2013.01);
(Continued)

(58) Field of Classification Search
None
See application file for complete search history.

(56) References Cited

U.S. PATENT DOCUMENTS

| 5,434,388 | A | * | 7/1995 | Kralik | F24H 1/121 219/522 |
| 5,714,738 | A | * | 2/1998 | Hauschulz | F16L 53/35 219/535 |
| 5,862,303 | A | * | 1/1999 | Adar | F16L 47/03 148/403 |
| 6,145,787 | A | * | 11/2000 | Rolls | B64D 15/12 219/545 |

(Continued)

FOREIGN PATENT DOCUMENTS

CN 201191920 Y * 2/2009 ............... H05B 3/34

OTHER PUBLICATIONS

CN-201191920Y, Huang, Feb. 2009, Bib. data sheet with abstract.*

Primary Examiner — Joseph M Pelham
(74) Attorney, Agent, or Firm — Burris Law, PLLC

(57) ABSTRACT

An electrical heating device for medical equipment is provided. The electrical heating device includes a conducting body forming a channel therethrough for fluid travel, a base dielectric layer disposed on the conducting body, a heater surrounding the base dielectric layer and the conducting body, a top dielectric layer disposed on the heater, and a protection housing that is preformed and that defines a cavity to receive the top dielectric layer and the heater in the cavity. The base dielectric layer and the top dielectric layer jointly enclose the heater. At least one of the base dielectric layer and the top dielectric layer has a radial portion at a side of the heater such that the radial portion surrounds a portion of the base layer dielectric that is sandwiched between the heater and the conducting body and no portion of the heater is exposed from the base dielectric layer and the top dielectric layer. The protection housing defines side pieces that are in direct contact with the conducting body.

20 Claims, 8 Drawing Sheets

Related U.S. Application Data

(60) Provisional application No. 61/328,697, filed on Apr. 28, 2010.

(51) Int. Cl.
*A61M 1/16* (2006.01)
*A61M 5/44* (2006.01)
*H05B 3/58* (2006.01)
A61F 7/00 (2006.01)
A61M 1/14 (2006.01)

(52) U.S. Cl.
CPC ............... *A61F 7/007* (2013.01); *A61M 1/14* (2013.01); *A61M 1/1621* (2014.02); *H05B 2203/021* (2013.01)

(56) References Cited

U.S. PATENT DOCUMENTS

| | | | |
|---|---|---|---|
| 2006/0237441 A1* | 10/2006 | Fujimura | H05B 3/04 219/531 |
| 2007/0086759 A1* | 4/2007 | Russegger | B29C 45/2737 392/473 |
| 2008/0021377 A1* | 1/2008 | Kienman | A61M 1/1696 604/29 |
| 2009/0010627 A1* | 1/2009 | Lindsay | A61M 1/1656 392/466 |
| 2009/0012655 A1* | 1/2009 | Kienman | A61M 1/28 700/300 |
| 2010/0046934 A1* | 2/2010 | Johnson | F24H 1/121 392/480 |

* cited by examiner

FLOW THROUGH HEATER

CROSS-REFERENCE TO RELATED APPLICATIONS

This application is a continuation application of U.S. Ser. No. 13/096,993, filed Apr. 28, 2011, which claims the benefit of provisional application Ser. No. 61/328,697, filed on Apr. 28, 2010, the contents of which are incorporated herein by reference in their entirety.

FIELD

The present disclosure relates generally to heaters, and more particularly to heaters for medical devices such as dialysis equipment.

BACKGROUND

The statements in this section merely provide background information related to the present disclosure and may not constitute prior art.

Heaters have been used in medical applications, such as dialysis equipment to heat fluids. Medical applications for heaters typically abide by certain standards to guarantee electrical safety for patients and operators of the medical equipment. Typically, medical applications follow one of three types of electrical safety standards. These are Type B, BF, and CF (F stands for floating). Type B provides basic protection against electrical shock and typically includes a direct ground. Type BF typically provides a greater degree of protection from electrical shock than Type B, because it uses a floating circuit with respect to the device ground. In other words, Type BF devices have double insulation without grounding of the device. The floating circuit removes the conduction of functional currents through the body in the event that the device is not properly grounded and the patient becomes the grounder. Type CF provides the highest degree of protection from electrical shock and is typically used in cardiac applications. Type CF also uses a floating circuit with double insulation and without grounding. The difference between BF and CF devices is the maximum allowed patient leakage current. Type CF (lowest leakage current) devices are necessary for application parts that are used near the heart.

For dialysis equipment, a heater is typically used to heat up dialysis liquids. The heater may be a flow through heater that includes a housing and a cartridge heater that is immersed within the dialysis fluid, such as the dialysate. Cartridge heaters meet Type B electrical standards, and therefore, it is essential that they are properly grounded. While the heater can be properly grounded in clinical settings, such as hospitals, proper grounded cannot be ensured for home dialysis applications.

SUMMARY

In one form, an electrical heating device for medical equipment includes a conducting body forming a channel therethrough for fluid travel, a base dielectric layer disposed on the conducting body, a heater surrounding the base dielectric layer and the conducting body, a top dielectric layer disposed on the heater, and a protection housing that is preformed and that defines a cavity to receive the top dielectric layer and the heater in the cavity. The base dielectric layer and the top dielectric layer jointly enclose the heater. At least one of the base dielectric layer and the top dielectric layer has a radial portion at a side of the heater such that the radial portion surrounds a portion of the base layer dielectric that is sandwiched between the heater and the conducting body and no portion of the heater is exposed from the base dielectric layer and the top dielectric layer. The protection housing defines side pieces that are in direct contact with the conducting body.

In another form, an electrical heating device includes a body, an insulating material disposed proximate the body, the insulating material being in the form of a base layer dielectric, a heater disposed proximate the base layer dielectric, a top dielectric layer disposed proximate the heater, and a protection housing that is preformed and that defines a cavity to receive the heater, the top dielectric layer and the base dielectric. The base layer dielectric and the top dielectric layer cooperate to encapsulate the heater. At least one of the base layer dielectric and the top dielectric layer has a radial portion at a side of the heater such that the radial portion surrounds a portion of the base layer dielectric that is sandwiched between the heater and the body and no portion of the heater is exposed from the base layer dielectric and the top dielectric layer. The base layer dielectric and the top dielectric layer are disposed within the cavity of the protection housing. The protection housing defines side pieces that are in direct contact with the conducting body.

In still another form, an electrical heating device is provided that includes a body, an insulating material disposed proximate the body, the insulating material being in the form of a base layer dielectric, a heater disposed proximate the base layer dielectric, a top dielectric layer disposed proximate the heater, and a protection housing surrounding the heater. The base layer dielectric and the top dielectric layer cooperate to encapsulate the heater, the base layer dielectric and the top dielectric layer being disposed within the protection housing.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
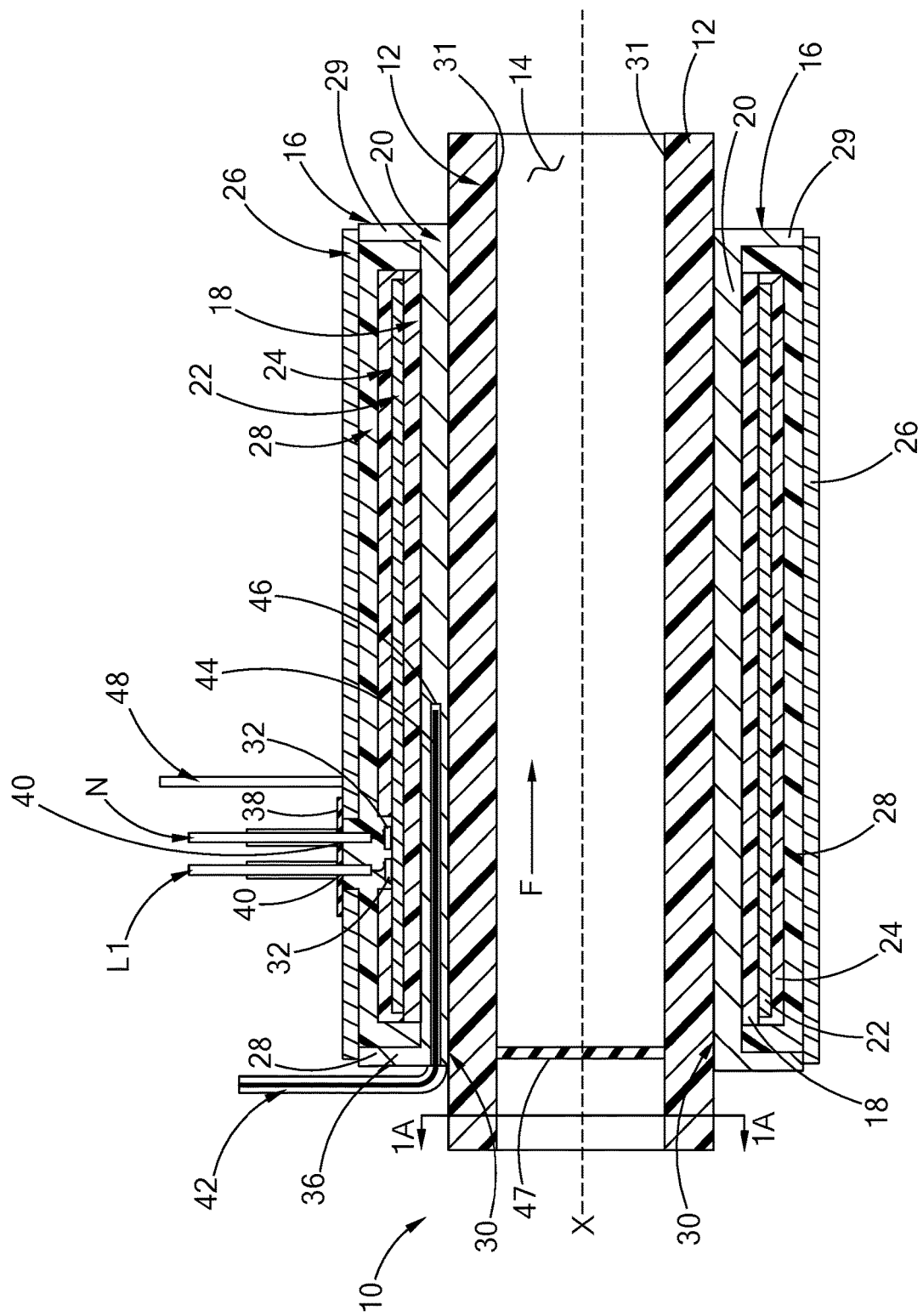
FIG. 1 is a cross-sectional view of an electrical heating device constructed in accordance with the principles of the present disclosure.

Referring to FIG. 1, an electrical heating device for medical equipment in accordance with the principles of the present disclosure is illustrated and generally indicated by reference numeral 10. The electrical heating device 10 has an insulating body 12, or tube, forming a channel 14 therethrough for fluid travel. For example, if used with dialysis equipment, the dialysis liquid, such as dialysate, may flow through the channel 14 generally in a direction F as indicated in FIG. 1. In this example, the insulating body 12 has a right circular cylindrical shape, and the channel 14 also has a right circular cylindrical shape for fluid to flow through. The heating device 10 may be fluidly connected to medical equipment, such as dialysis equipment, in any suitable manner, such as through the use of Swagelok fittings or other threaded fittings, by way of example.

The insulating body 12 is formed of an insulating material, such as a sintered ceramic, for example $Al_2O_3$ or as another example borosilicate glass. The insulating body 12 could have an electrical breakdown voltage between about 1000 VAC and 4000 VAC by way of example. Further, the insulating body 12 could have a leaking current between about 10 pA and 1000 pA at application temperature and using a measurement voltage of about 10%. In some forms, the insulating body 12 could be free from hygroscopic properties. Likewise, the insulating body 12 could be constructed to be biocompatible and consistent against bases and acids, however, it should be understood that the insulating body 12 could have other constructions without falling beyond the spirit and scope of the present disclosure.

An insulating material surrounds the insulating body 12. In this example, the insulating material is in the form of a base layer dielectric 18, which is disposed radially outward from the insulating body 12 and the central axis X of the heating device 10.

A heater 22 is disposed on the base layer dielectric 18 and surrounds the base layer dielectric 18, an inner portion 20 of a protection housing 16 (described in further detail below), and the insulating body 12. A top layer dielectric 24 is disposed over the heater 22. The base layer dielectric 18 and the top layer dielectric 24 cooperate to encapsulate the heater 22.

A protection housing 16 surrounds the insulating body 12. An outer portion 26 of the protection housing 16 surrounds the heater 22 and dielectrics 18, 24. The outer portion 26 cooperates with an inner portion 20 of the protection housing 16 to encapsulate the dielectrics 18, 24 and the heater 22; therefore, the protection housing 16 is located on both sides of the heater 22. More particularly, the inner portion 20 of the protection housing 16 is disposed on the insulating body 12, and the base layer dielectric 18 is disposed directly on the inner portion 20 of the protection housing 16.

An electrically and thermally insulating compound 28 is disposed within the cavity of the protection housing 16 formed by the inner and outer portions 20, 26 of the protection housing 16. The compound 28 surrounds the heater 22, the top layer dielectric 24, and the base layer dielectric 18. The protection housing 16 separates the dielectrics 18, 24 and the heater 22 from the insulating body 12. The protection housing 16 provides for mechanical protection for the heater 22, the dielectrics 18, 24, and the compound 28 that surrounds the heater 22 and dielectrics 18, 24 because the dielectrics 18, 24, heater 22, and compound 28 are each disposed within the enclosed cavity area within the protection housing 16. This separation helps protect against cracking of the dielectrics 18, 24 if the insulating body 12 breaks for any reason and avoids that fluid comes in contact with the electrical active heater 22.

The protection housing 16 may be electrically conductive. For example, the protection housing 16 may be formed of stainless steel, by way of example. Other suitable materials include, but are not limited to, nickel-plated copper, aluminum, stainless steel, mild steels, tool steels, refractory alloys, and aluminum nitride, among others. In some forms, the protection housing 16 is consistent against acids and bases, even though under normal conditions, the protection housing 16 does not contact the dialysis liquid that flows through the channel 14 of the insulating body 12.

The protection housing 16 may be constructed using laser welded turning parts or drawn tubes in combination with turning parts, by way of example. The outer and inner portions 26, 20, and any other parts of the protection housing 16, may be joined through laser welding or soldering, by way of example. In FIG. 1, the inner portion 20 of the protection housing 16 is shown to have flanges 29, which extend radially outwardly from the central axis X of the heating device 10 and which are connected to the outer portion 26 of the protection housing 16. It should be understood, however, that the flanges 29 could be formed as part of the outer portion 26 instead of the inner portion 20, or the flanges 29 could be formed separately from both the outer and inner portions 26, 20 and connected to the outer and inner portions 26, 20 to form the protection housing 16.

To connect the protection housing 16 to the insulating body 12, various methods may be used. For example, the insulating body 12 may be slid into a passageway formed by the inner sides 30 of the inner portion 20 of the protection housing 16 and a force fit, such as shrinking or clamping, could be used to join the protection housing 16 and the insulating body 12. Alternatively, or in addition, the protection housing 16 may be connected to the insulating body 12 by way of soldering (metal or glass solder), gluing (organic or inorganic), welding (laser or diffusion welding), or co-firing, or any other suitable method, without falling beyond the spirit and scope of the present invention.

In some forms, the protection housing 16 and the insulating body 12 have a holohedral contact therebetween. The holohedral contact allows accurate heat transfer from the heater 22 to reach the liquid flowing through the channel 14 of the insulating body 12.

The dielectrics 18, 24 may be applied by any possible layering technology or other suitable method. For example, each dielectric 18, 24 may be a layer formed through application or accumulation of a material to the inner portion 20 (for the base layer dielectric 18) or the heater 22 (for the top layer dielectric 24) using processes associated with thick film, thin film, thermal spraying, or sol-gel, among others.

These processes are also referred to as "layered processes" or "layering processes." Thick film processes may include, by way of example, screen printing, spraying, rolling, and transfer printing, among others. Thin film processes may include, by way of example, ion plating, sputtering, chemical vapor deposition (CVD), and physical vapor deposition (PVD), among others. Thermal spraying processes may include, by way of example, flame spraying, plasma spraying, wire arc spraying, and HVOF (High Velocity Oxygen Fuel), among others.

Similarly, in some forms, the heater 22 may be applied to the heating device 10 by a layering technology, such as those described above. For example, the heater 22 may be applied to the base layer dielectric 20 by thermal spraying. In the alternative the heater 22 could simply be a preformed tubular heater.

The electrically and thermally insulating compound 28 assists with providing temperature stability. It may be formed of any suitable materials, such as Silicone casting resin, Epoxy casting resin, and Polyurethane casting resin, by way of example.

The heater 22 may be connected to a pair of conductors 32, which are terminal pads that are further connected to a power source (not shown) through terminal wires or other electrical leads N and L1. It should be understood that the conductors 32 could take forms other than terminal pads, without departing from the spirit and scope of the present disclosure, so long as the heater 22 is electrically connected to a power source in another suitable manner. In one form, the conductors 32 could be omitted and the heater 22 could connect directly to the electrical leads N and L1. Although the electrical leads N and L1 are illustrated as extending radially outward from the heater 22 with regard to the central axis X of the heating device 10, it should be understood that the leads N, L1 could extend from the heater 22 in any suitable manner, such as axially parallel to the central axis X through an end 36 of the protection housing 16, by way of example.

In some forms, the leads N, L1 extend through a separate housing piece 38 of the protection housing 16. This allows the leads N, L1 to be connected to the heater 22 after the heater 22 is assembled inside the protection housing 16. The leads N, L1 may be guided through apertures 40 in the housing piece 38, and the housing piece 38 may be connected to the outer portion 26 of the protection housing 16 in any suitable manner, such as those described above with regard to connecting the outer and inner portions 26, 20 of the protection housing 16.

In some forms, a temperature sensor 42 extends from the protection housing 16. An end 44 of the temperature sensor 42 is disposed within the protection housing 16. The end 44 of the temperature sensor 42 may be surrounded by insulation material 46 separating the end 44 of the temperature sensor 42 from the protection housing 16 and insulating it therefrom for electrical safety. The position of the temperature sensor 42 may vary, without falling beyond the spirit and scope of the present disclosure.

The temperature sensor 42 is shown axially mounted in FIG. 1, but it should be understood that it could extend in another other suitable direction, without falling beyond the spirit and scope of the present disclosure. For example, the temperature sensor 42 can be radially mounted and extend in a radially outward direction from the central axis X of the heating device 10, similarly to the leads N, L1.

The temperature sensor 42 could be of any suitable type, such as an RTD (resistive temperature detector), a thermocouple, or a thermistor, such as an NTC (negative temperature coefficient) thermistor, by way of example. More than one temperature sensor 42 could be mounted to the heating device 10 for a redundant temperature measurement system.

To provide for over-temperature protection, the temperature sensor 42 may be provided in combination with a temperature controller (not shown). A thermal switch (not shown), such as a fuse or bimetallic switch by way of example, may be mounted on an outer or inner surface of the protection housing 16. If the switch is mounted on the inner surface of the protection housing 16, it may be embedded in the compound 28. Other control systems may include a two wire control system or a self-regulating heating layer material, such as barium titanate. Any suitable control system could be used alone or in combination with another control system. In addition, to avoid overheating inside the equipment housing, an additional thermal insulation could be used. Such additional thermal insulation could be mounted on an outer surface of the protection housing 16 or inside the protection housing 16.

Figure 1A:
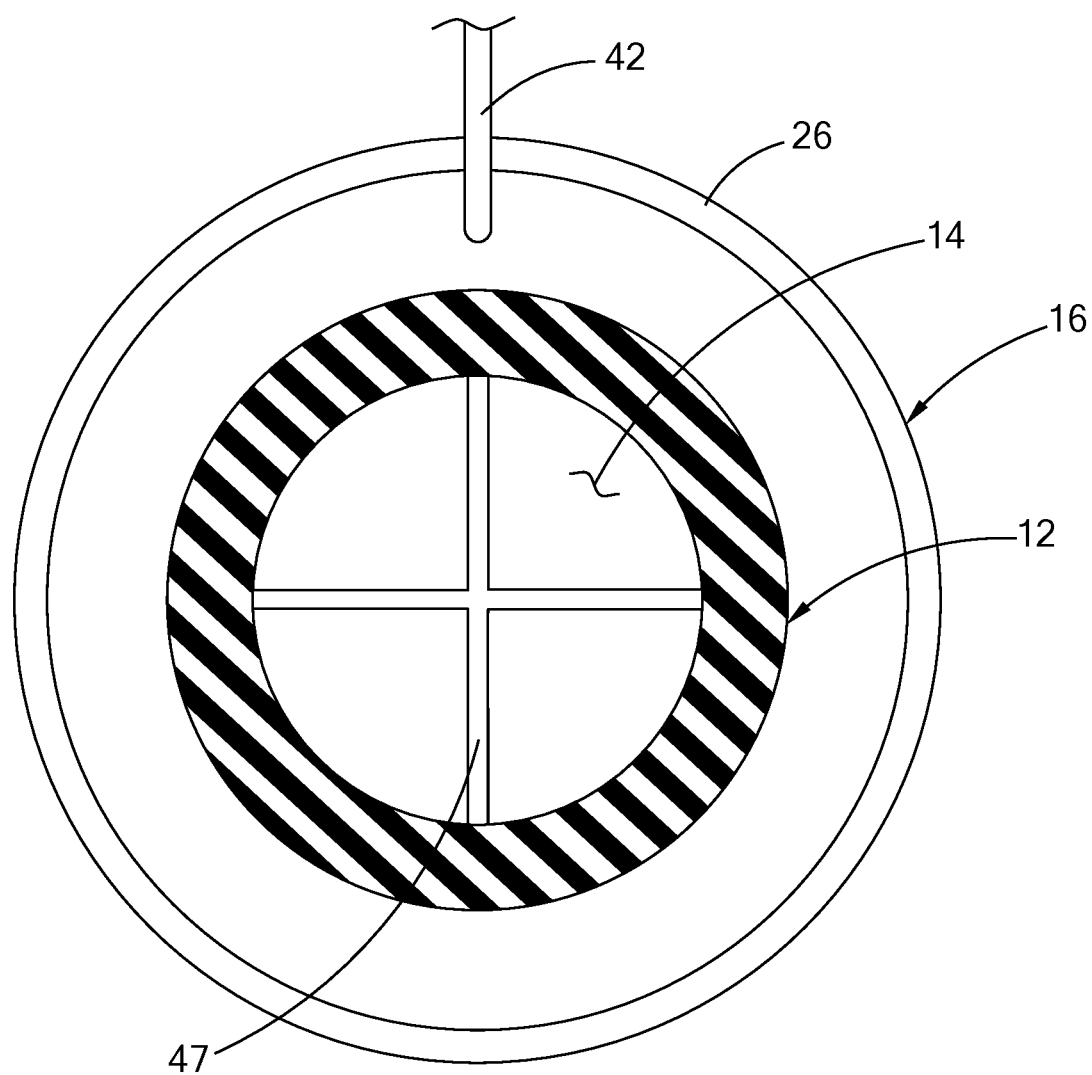
FIG. 1A is a cross-sectional view of an alternate form of the electrical heating device of FIG. 1, taken along the line 1A-1A.

Now with reference to FIGS. 1 and 1A, the electrical heating device may include one or more baffles 47 or other turbulence-inducing structures for inducing turbulent flow of the liquid flowing through the channel 14. The baffle 47 may be in any suitable form, such as a "T" shape shown in FIG. 1A, or it could be a bar, rod, or spring extending across or partially across the channel 14, by way of example. In addition, or in the alternative, the interior surface 31 of the insulating body 12 could have a corrugated, baffled, irregular surface, or other turbulence-inducing surface geometry (not shown) to induce turbulent flow of the liquid flowing through the channel 14. It should be understood that the specific configuration as illustrated herein should not be construed as limiting the scope of the present disclosure.

In some forms, the heating device 10 may also include a measurement circuit 48 electrically connected to the protection housing 16. The measurement circuit 48 may be configured to measure leakage current through the insulating body 12 and one or more of the dielectrics 18, 24. The leakage current may be checked while the heater 22 is in use or in constant periods, by way of example.

Figure 2A:
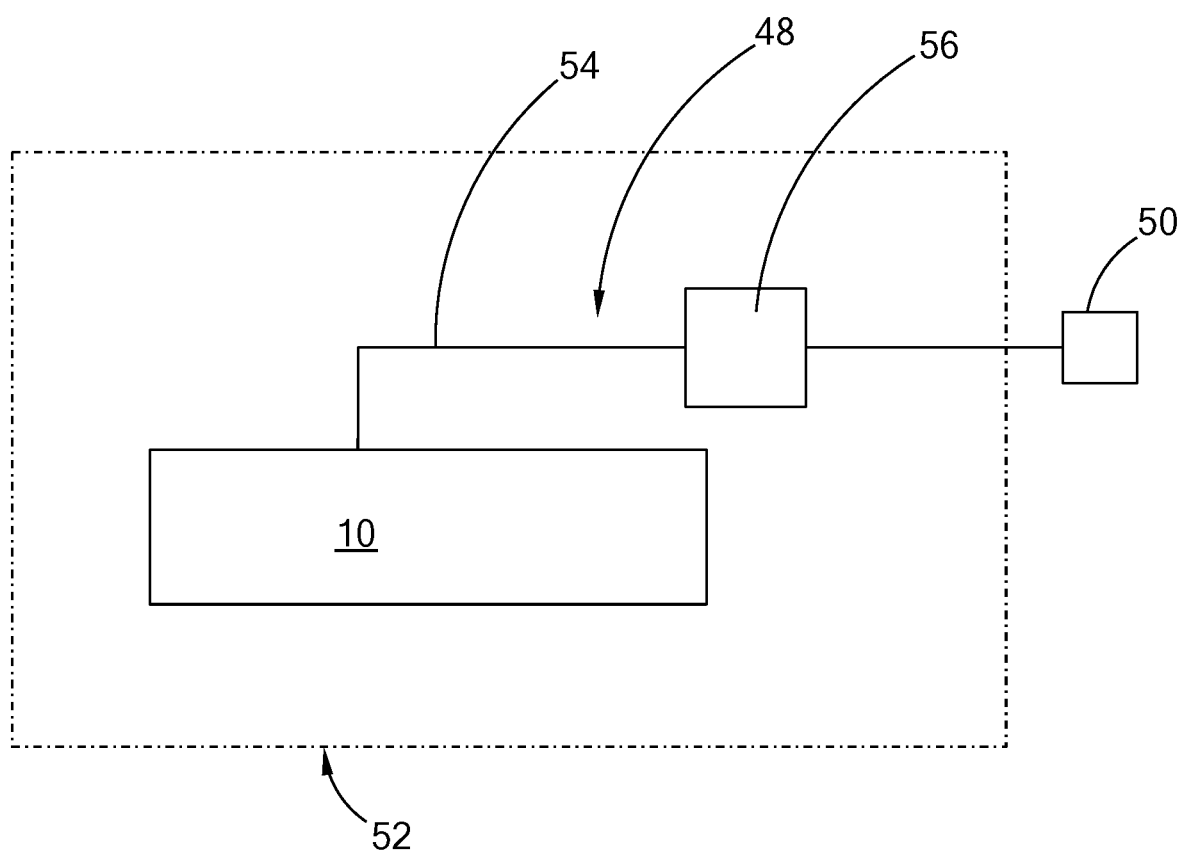
FIG. 2A is a schematic view of a measurement circuit for use with the electrical heating device of FIG. 1, displayed in accordance with the principles of the present disclosure.

Now with reference to FIG. 2A, an example of a measurement circuit 48 is illustrated. The measurement circuit 48 may include an interface 50 located outside of the dialysis equipment housing 52. The measurement lead 54 extends from the heating device 10 to an optocoupler 56 and out of the dialysis equipment 52 to the interface 50, to provide for galvanic isolation of the measurement circuit 48.

Figure 2B:
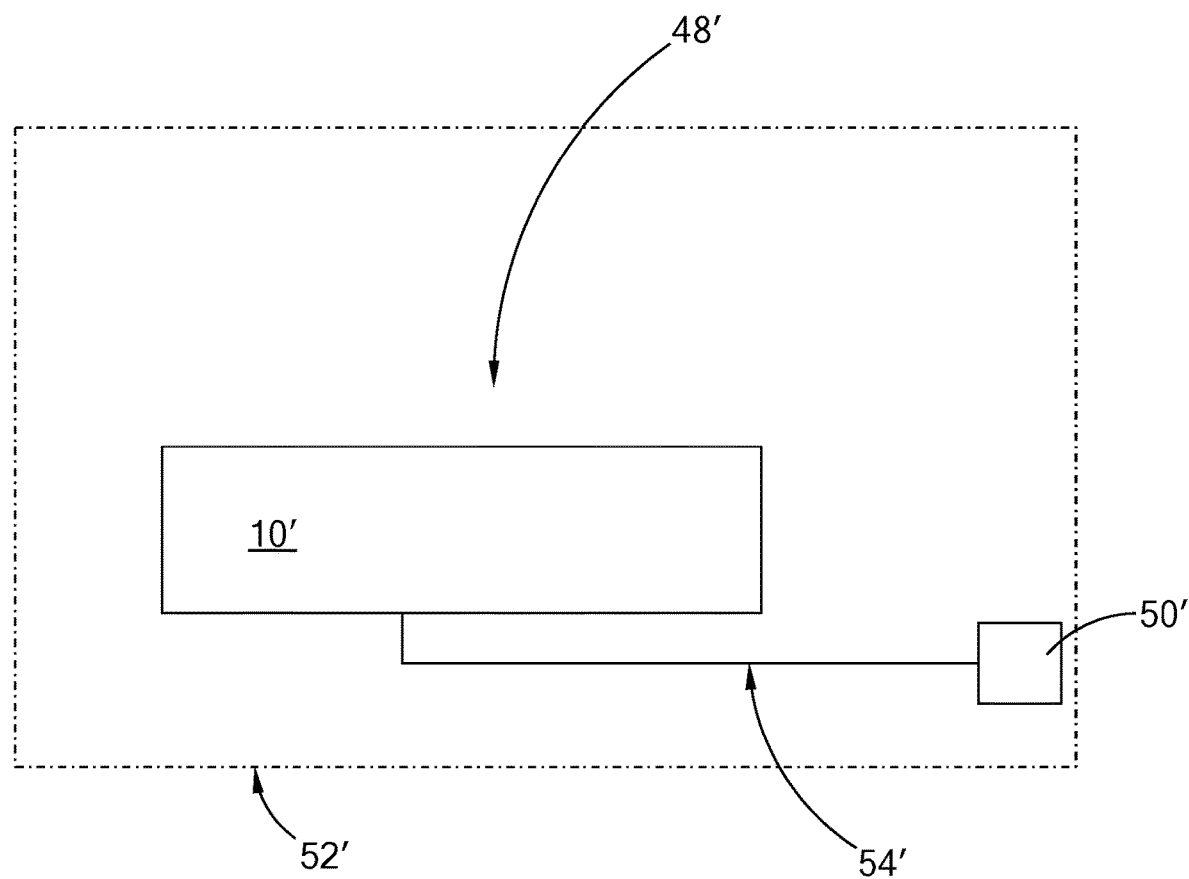
FIG. 2B is a schematic view of another measurement circuit for use with the electrical heating device of FIG. 1, displayed in accordance with the principles of the present disclosure.

Now with reference to FIG. 2B, another example of a measurement circuit 48' is illustrated. The measurement circuit 48' includes an interface 50' located within the dialysis equipment housing 52'. The measurement lead 54' extends from the heating device 10' to the interface 50' located inside the dialysis equipment 52', to provide a measurement circuit 48' without galvanic isolation.

The electrical heating device 10 may be provided to have a Type BF or a Type CF electrical safety rating, depending on the maximum leakage current to the patient. In some forms, a Type B electric safety rating may also be used.

Figure 3:
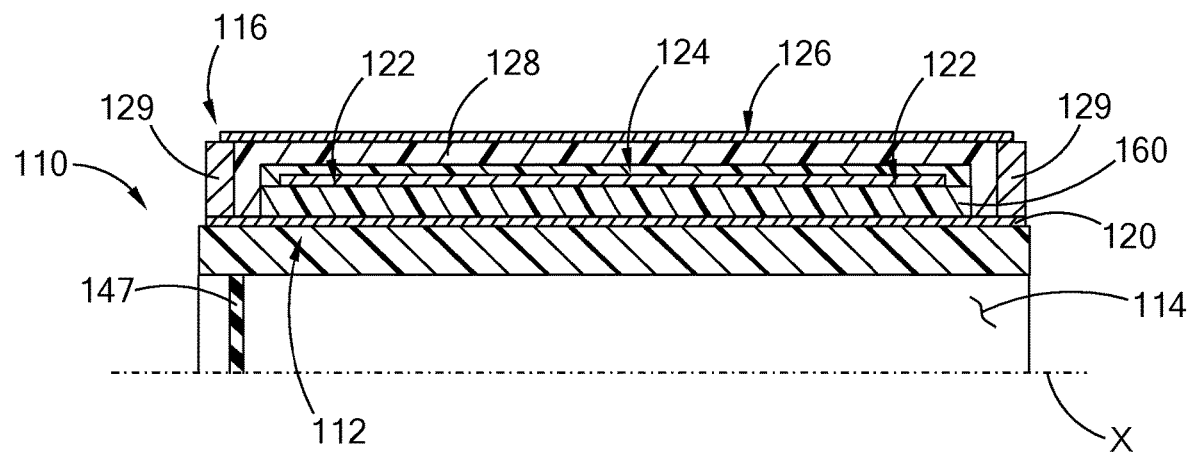
FIG. 3 is a cross-sectional view of a portion of another electrical heating device constructed in accordance with the principles of the present disclosure.

Now with reference to FIG. 3, another form of an electrical heating device within the spirit and scope of the present disclosure is illustrated and generally designated at reference numeral 110. Half of a cross-section of the electrical heating device 110 is shown, but it should be understood that the other half of the cross-section of the electrical heating device 110 would be identically present and mirrored across the central axis X.

Like the electrical heating device 10 hereinbefore described, the electrical heating device 110 of FIG. 3 also has a right circular cylindrical shape, however, it should be understood that other shapes could, such as cylinders other than right circular cylinders or rectangular shapes could be used without falling beyond the spirit and scope of the present disclosure.

The electrical heating device 110 has a primary insulating body 112 forming a channel 114 therethrough for fluid to travel, such as dialysis liquid. The primary insulating body 112 is formed of an insulating material and has properties as described above with respect to the insulating body 12 of FIG. 1. The primary insulating body 112 may also have a baffle 147 or other turbulence-inducing structure, as described above with respect to FIGS. 1 and 1A.

A conductive layer 120 is disposed around the primary insulating body 112. The conductive layer 120 is formed of an electrically conductive material. The conductive layer 120 may be formed by a layering process, such as thick film, thin film, or thermal spraying, by way of example. In some forms, the conductive layer 120 and the primary insulating body 112 have a holohedral contact therebetween to allow accurate heat transfer from the heater 122 to the liquid flowing through the channel 114 of the primary insulating body 112.

Insulating material, in the form of a secondary insulating body 160, surrounds the conductive layer 120 and the primary insulating body 112. The secondary insulating body 160, like the primary insulating body 112, may be formed of an insulating material, such as a sintered ceramic, for example $Al_2O_3$, or as an other example borsilicate glass and may have the properties described above with regard to the insulating body 12.

A heater 122 is disposed on the secondary insulating body 160 and surrounds the secondary insulating body 160. In this example, the heater 122 directly contacts the secondary insulating body 160. The conductive layer 120 and the secondary insulating body 160 are disposed between the primary insulating body 112 and the heater 122. The heater 122 may be constructed as described above with respect to the heater 22 of FIG. 1.

A dielectric 124 is disposed over the heater 122. The dielectric may be similar and applied similarly to the dielectrics 18, 24 described above with respect to FIG. 1. The dielectric 124 and the secondary insulating body 160 cooperate to encapsulate the heater 122.

An electrically and thermally insulating compound 128 is disposed around the dielectric 124, the heater 122, and the secondary insulating body 160. The compound 128 may be similar to the compound 28 described above with respect to FIG. 1.

A protection housing 116 surrounds the heater 122, the compound 128, the dielectric 124, the conductive layer 120, and the primary and secondary insulating bodies 112, 160. The dielectric 124 is disposed between the heater 122 and the protection housing 116.

In this example, the protection housing 116 includes an outer portion 126 and electrically conductive side pieces 129 that connect the outer portion 126 of the protection housing 116 to the conductive layer 120 to form a cavity in which the secondary insulating body 160, the heater 122, the dielectric 124, and the compound 128 are disposed. In other words, the protection housing 116 and the conductive layer 120 cooperate to encapsulate the secondary insulating body 160, the heater 122, the dielectric 124, and the compound 128. The outer portion 126 and the side pieces 129 of the protection housing 116 may be constructed of electrically conductive material, such as that described above with respect to the protection housing 16 of FIG. 1. Likewise, the conductive layer 120, the side pieces 129, and the outer portion 126 of the protection housing 116 may be connected as described above with regard to the protection housing 16, such as by laser welding or soldering.

The heater 122 may be connected to a power source by a pair of electrical leads (not shown), similarly to the connection shown in FIG. 1, by way of example. In some forms, the leads may extend through a separate housing piece (not shown), such as the housing piece 38 of the protection housing 16 shown in FIG. 1. One or more temperature sensors (not shown) may also be employed, such as the temperature sensor 42 shown and described with respect to FIG. 1. Likewise, a measurement circuit could be used, such as the measurement circuits 48, 48' shown and described with respect to FIGS. 2A and 2B, to measure leakage current through the primary insulating body 112, the secondary insulating body 160, and/or the dielectric 124.

Thus, the electrical heating device 110 may be provided having a Type BF or a Type CF electrical safety rating, depending on the maximum leakage current to the patient. In some forms, a Type B electric safety rating may also be used.

Figure 4:
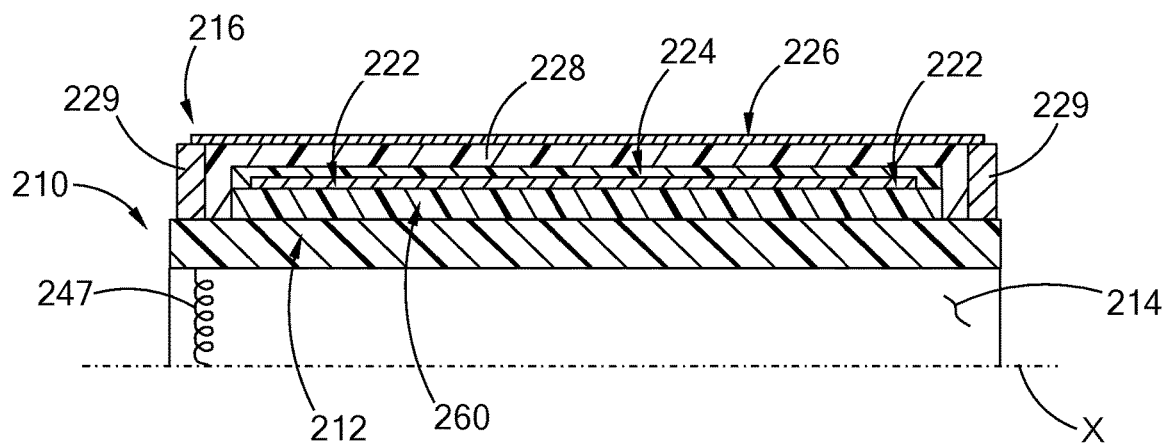
FIG. 4 is a cross-sectional view of a portion of yet another electrical heating device constructed in accordance with the principles of the present disclosure.

Now with reference to FIG. 4, another form of an electrical heating device within the spirit and scope of the present disclosure is illustrated and generally designated at reference numeral 210. Half of a cross-section of the electrical heating device 210 is shown, but it should be understood that the other half of the cross-section of the electrical heating device 210 would be identically present and mirrored across the central axis X.

Like the electrical heating devices 10, 110 hereinbefore described, the electrical heating device 210 of FIG. 4 also has a right circular cylindrical shape, however, it should be understood that other shapes, such as cylinders other than right circular cylinders or rectangular shapes, could be used without falling beyond the spirit and scope of the present disclosure.

The electrical heating device 210 has a primary insulating body 212 forming a channel 214 therethrough for fluid travel, such as dialysis liquid. The primary insulating body 212 is formed of an insulating material and has properties as described above with respect to the insulating body 12 of FIG. 1. The primary insulating body 212 may also have a spring 247 extending across the channel 214 to induce turbulent flow of fluid. The heating device 210 could also or alternatively have other turbulence-inducing structures, as described above, by way of example.

A secondary insulating body 260 surrounds the primary insulating body 212. The secondary insulating body 260, like the primary insulating body 212, may be formed of an insulating material, such as a sintered ceramic, for example $Al_2O_3$, or as another example borosilicate glass, and may have the properties described above with regard to the insulating body 12.

A heater 222 is disposed on the secondary insulating body 260 and surrounds the secondary insulating body 260. The heater 222 directly contacts the secondary insulating body 260. As such, the secondary insulating body 260 is disposed between the primary insulating body 212 and the heater 222. The heater 222 may be constructed in any suitable manner, such as the examples described above with respect to the heater 22 of FIG. 1.

A dielectric 224 is disposed over the heater 222. The dielectric 224 may be similar and applied similarly to the dielectrics 18, 24 described above with respect to FIG. 1.

The dielectric 224 and the secondary insulating body 260 cooperate to encapsulate the heater 222.

An electrically and thermally insulating compound 228 is disposed around and surrounds the dielectric 224, the heater 222, and the secondary insulating body 260. The compound 228 may be similar to the compound 28 described above with respect to FIG. 1.

A protection housing 216 surrounds the heater 222, the compound 228, the dielectric 224, and the primary and secondary insulating bodies 212, 260. The dielectric 224 is disposed between the heater 222 and the protection housing 216.

In this example, electrically conductive side pieces 229 connect the outer portion 226 of the protection housing 216 to the primary insulating body 212 to form a cavity in which the secondary insulating body 260, the heater 222, the dielectric 224, and the compound 228 are disposed. In other words, the protection housing 216 and the primary insulating body 212 cooperate to encapsulate the secondary insulating body 260, the heater 222, the dielectric 224, and the compound 228. The outer portion 226 of the protection housing 216 and the side pieces 229 may be constructed of electrically conductive material, such as that described above with respect to the protection housing 16 of FIG. 1.

The heater 222 may be connected to a power source by a pair of electrical leads (not shown), similarly to the connection shown in FIG. 1, by way of example. In some forms, the leads may extend through a separate housing piece (not shown), such as the housing piece 38 of the protection housing 16 shown and described with respect to FIG. 1.

The electrical heating device 210 may be provided having a Type BF or a Type CF electrical safety rating, depending on the maximum leakage current to the patient. In some forms, a Type B electric safety rating may also be used.

Figure 5:
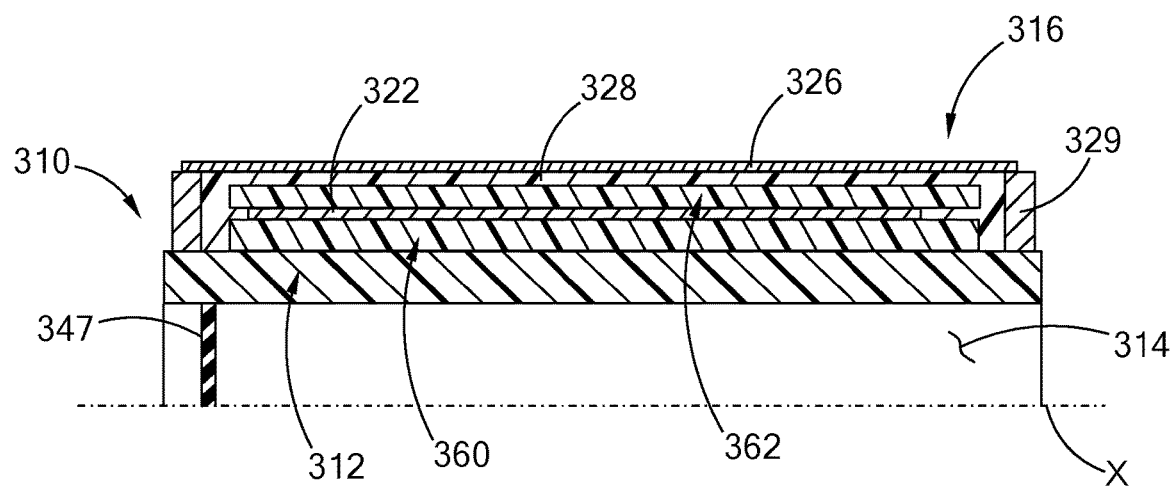
FIG. 5 is a cross-sectional view of a portion of still another electrical heating device constructed in accordance with the principles of the present disclosure.

Now with reference to FIG. 5, another form of an electrical heating device within the spirit and scope of the present disclosure is illustrated and generally designated at reference numeral 310. Half of a cross-section of the electrical heating device 310 is shown, but it should be understood that the other half of the cross-section of the electrical heating device 310 would be identically present and mirrored across the central axis X.

Like the electrical heating devices 10, 110, 210 hereinbefore described, the electrical heating device 310 of FIG. 5 also has a right circular cylindrical shape, however, it should be understood that other shapes could be used, such as cylinders other than right circular cylinders or rectangular shapes, without falling beyond the spirit and scope of the present disclosure.

The electrical heating device 310 has a primary insulating body 312 forming a channel 314 therethrough for fluid travel, such as dialysis liquid. The primary insulating body 312 is formed of an insulating material and has properties as described above with respect to the insulating body 12 of FIG. 1. The primary insulating body 312 may also have a baffle 347 located in the channel 314 to induce turbulent flow of fluid. The heating device 310 could also or alternatively have other turbulence-inducing structures, as described above, by way of example.

A secondary insulating body 360 surrounds the primary insulating body 312. A heater 322 is disposed on the secondary insulating body 360 and surrounds the secondary insulating body 360. The heater 322 directly contacts the secondary insulating body 360, and the secondary insulating body 360 is disposed between the primary insulating body 312 and the heater 322. The heater 322 may be constructed as described above with respect to the heater 22 of FIG. 1.

A top insulating body 362 is disposed on the heater 322. The top insulating body 362 may be similar to the primary and secondary insulating bodies 312, 360. For example, each of the insulating bodies 312, 360, 362, may be formed of an insulating material, such as a sintered ceramic, for example, an $Al_2O_3$ borosilicate glass, and may have the properties described above with regard to the insulating body 12.

An electrically and thermally insulating compound 328 is disposed around and surrounds the top insulating body 362, the heater 322, and the secondary insulating body 360. The compound 328 may be similar to the compound 28 described above with respect to FIG. 1. The top insulating body 362, the secondary insulating body 360, and the compound 328 cooperate to encapsulate the heater 322.

A protection housing 316 surrounds the heater 322, the compound 328, and the secondary and top insulating bodies 360, 362. In this example, electrically conductive side pieces 329 connect the outer portion 326 of the protection housing 316 to the primary insulating body 312 to form a cavity in which the secondary insulating body 360, the heater 322, the top insulating body 362, and the compound 228 are disposed. In other words, the protection housing 316 and the primary insulating body 312 cooperate to encapsulate the secondary and top insulating bodies 360, 362, the heater 322, and the compound 328. The outer portion 326 of the protection housing 316 and the side pieces 329 may be constructed of electrically conductive material, such as that described above with respect to the protection housing 16 of FIG. 1.

The heater 322 may be connected to a power source by a pair of electrical leads (not shown), similarly to the connection shown in FIG. 1, by way of example. In some forms, the leads may extend through a separate housing piece (not shown), such as the housing piece 38 of the protection housing 16 shown in FIG. 1.

The electrical heating device 310 may be provided having a Type BF or a Type CF electrical safety rating, depending on the maximum leakage current to the patient. In some forms, a Type B electric safety rating may also be used.

Figure 6:
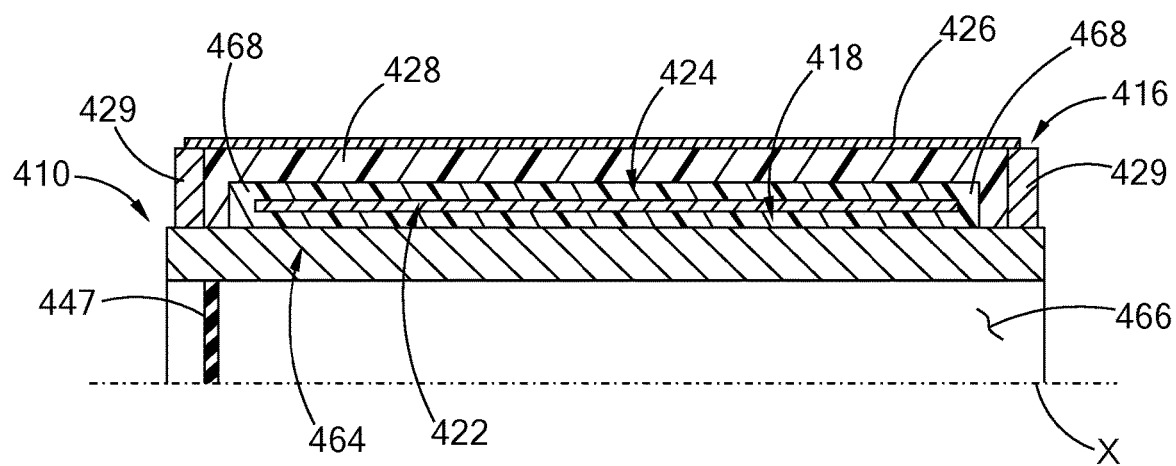
FIG. 6 is a cross-sectional view of a portion of still another electrical heating device constructed in accordance with the principles of the present disclosure.

Now with reference to FIG. 6, another form of an electrical heating device within the spirit and scope of the present disclosure is illustrated and generally designated at reference numeral 410. Half of a cross-section of the electrical heating device 410 is shown, but it should be understood that the other half of the cross-section of the electrical heating device 410 would be identically present and mirrored across the central axis X.

Like the electrical heating devices 10, 110, 210, 310 hereinbefore described, the electrical heating device 410 of FIG. 6 also has a right circular cylindrical shape, however, it should be understood that other shapes, such as cylinders other than right circular cylinders or rectangular shapes, could be employed without falling beyond the spirit and scope of the present disclosure.

The electrical heating device 410 has a conducting body 464 forming a channel 466 therethrough for fluid travel, such as dialysis liquid. The conducting body 464 is formed of an electrically conductive material, for example, a metal, such as stainless steel. Any other suitable electrically conductive material could also or alternatively be employed.

The conducting body 464 may also have a baffle 447 located in the channel 466 to induce turbulent flow of liquid. The heating device 410 could also or alternatively have other turbulence-inducing structures, as described above, by way of example.

A base dielectric layer 418 is disposed on the conducting body 464. The base dielectric layer 418 may be similar and applied similarly to the dielectrics 18, 24 described above with respect to FIG. 1.

A heater 422 is disposed on the base dielectric layer 418. The heater 422 surrounds the base dielectric layer 418 and the conducting body 464. The heater 422 may be constructed as described above with respect to the heater 22 of FIG. 1.

A top dielectric layer 424 is disposed over the heater 422. The top dielectric layer 424 may also be similar and applied similarly to the dielectrics 18, 24 described above with respect to FIG. 1. The top and base dielectric layers 424, 418 cooperate to encapsulate the heater 422 as shown in FIG. 6. Each of the top and base dielectric layers 424, 418 extend longitudinally farther along the length of the heating device 410 than the heater 422 extends. As such, the dielectric layers 418, 424 contact each other at edges 468 to surround and encapsulate the heater 422.

An electrically and thermally insulating compound 428 is disposed around the dielectric layers 418, 424 and the heater 422. The compound 428 may be similar to the compound 28 described above with respect to FIG. 1.

A protection housing 416 surrounds the heater 422, the compound 428, the top dielectric layer 424, the base dielectric layer 418, and the conducting body 464. The top dielectric layer 424 is disposed between the heater 422 and an outer portion 426 of the protection housing 416.

In this example, the protection housing 416 includes the electrically conductive outer portion 426 and electrically conductive side pieces 429 that connect the outer portion 426 of the protection housing 416 to the conducting body 464 to form a cavity in which the heater 422, the dielectric layers 418, 424, and the compound 428 are disposed. In other words, the protection housing 416 and the conducting body 464 cooperate to encapsulate the heater 422, the top and base dielectric layers 424, 418 and the compound 428. The outer portion 426 and the side pieces 429 of the protection housing 416 may be constructed of any suitable electrically conductive material, such as that described above with respect to the protection housing 16 of FIG. 1. Likewise, the conducting body 464, the side pieces 429, and the outer portion 426 of the protection housing 416 may be connected as described above with regard to the protection housing 16, such as by laser welding or soldering.

The heater 422 may be connected to a power source by a pair of electrical leads (not shown), similarly to the connection shown in FIG. 1, by way of example, although any other suitable connection may be used, without falling beyond the spirit and scope of the present disclosure. In some forms, the leads may extend through a separate housing piece (not shown), such as the housing piece 38 shown in FIG. 1. One or more temperature sensors (not shown) may also be employed, such as the temperature sensor 42 shown and described with respect to FIG. 1.

The conducting body 464 is configured to be grounded. Thus, the electrical heating device 410 may be provided having a Type B electric safety rating.

Figure 7:
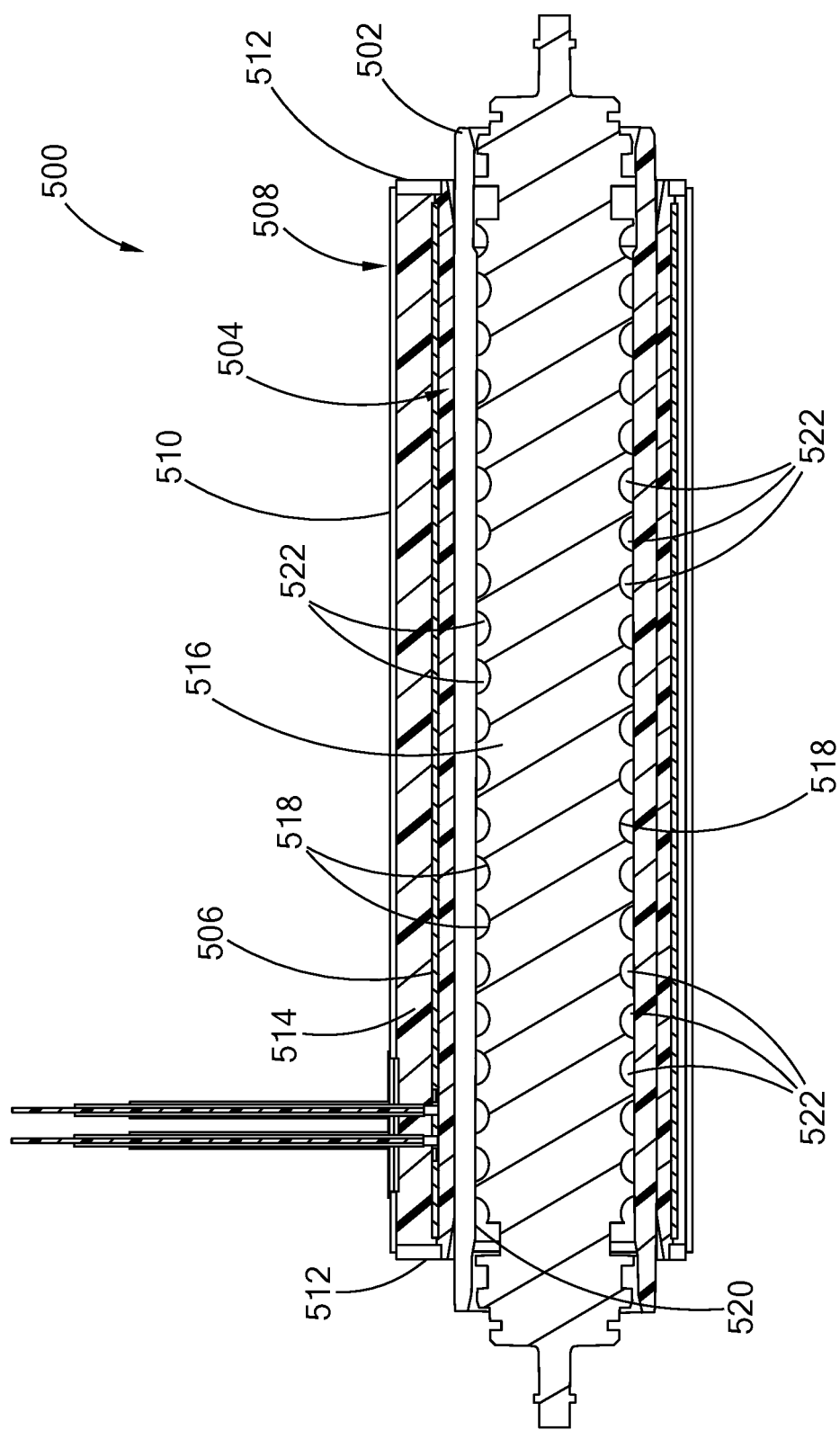
FIG. 7 is a cross-sectional view of still another electrical heating device constructed in accordance with the principles of the present disclosure.

Referring to FIG. 7, another form of an electrical heating device 500 constructed in accordance with the principles of the present disclosure includes an insulating body 502 defining a longitudinal passageway, a substrate 504 disposed on and surrounding the insulating body 502, a heater 506 disposed on and surrounding the substrate 504, and a protection housing 508. The protection housing 508 includes an outer portion 510 and side pieces 512 that connect the outer portion 510 to the secondary insulating substrate 504 to form a cavity in which the heater 506 and an electrically and thermally insulating compound 514 are disposed. Therefore, the protection housing 508 and the substrate 504 cooperate to encapsulate the heater 506 and the compound 514. The substrate 504 is made of a solid material and may be electrically insulating or non-insulating. Similarly, the heater 506 may be a thermally sprayed heater as described with regard to FIGS. 1 to 6. The protection housing 508 may be constructed and connected to the insulating body 502 or the substrate 504 in any manner as described with regard to FIGS. 1 to 6.

The electrical heating device 500 further includes a baffle 516 in the form of a cylindrical core body. The baffle 516 may be formed of electrically insulating or non-insulating material. The baffle 516 defines a plurality of waved portions 518 on the peripheral surface and is configured such that when the baffle 516 is inserted into the longitudinal passageway of the insulating body 502, the waved portions 518 and the inner surface 520 of the insulating body 502 jointly form a plurality of fluid channels 522 to allow fluid, such as dialysis liquid, to flow through.

Figure 8:
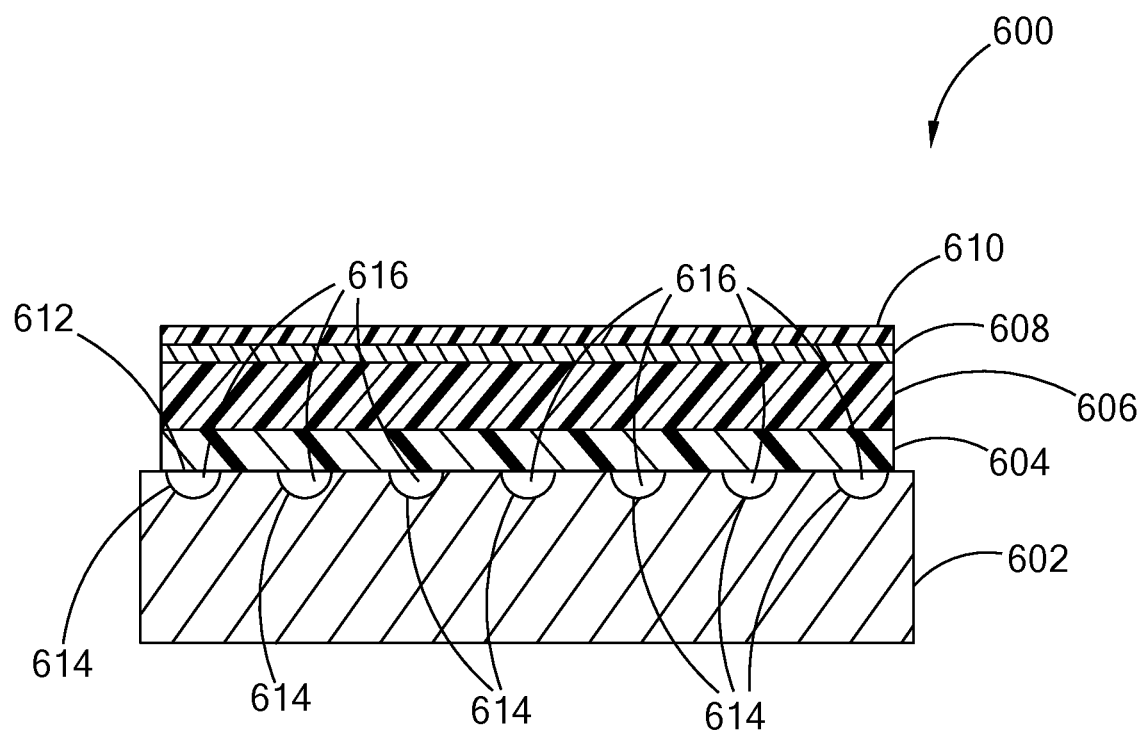
FIG. 8 is a cross-sectional view of still another electrical heating device constructed in accordance with the principles of the present disclosure.

Referring to FIG. 8, another form of an electrical heating device 600 constructed in accordance with the principles of the present disclosure has a plate configuration. More specifically, the electrical heating device 600 includes a plate body 602, an insulating material in the form of a base dielectric layer 604 disposed on the plate body 602, a substrate 606 disposed on the base dielectric layer 604 and a heater 608 disposed on the substrate 606. Optionally, another insulating material in the form of a top dielectric layer 610 may be formed on the heater 608.

The plate body 602 includes a flat side surface 612 proximate the base dielectric layer 604. A plurality of openings 614 are formed through the flat side surface 612. The base dielectric layer 604 and the plate body 602 jointly define a plurality of fluid channels 616 to allow fluid, such as dialysis liquid, to flow through. The plate body 602 may be formed of an electrically insulating material, such as ceramics, or an electrically non-insulating material.

The substrate 606 is disposed on the base dielectric layer 604 and is made of a solid material separate from the base dielectric layer 604. The substrate 606 may be made of an insulating material or a non-insulating material. The substrate 606 functions as a substrate for the heater 608, which may be a thermally-sprayed heater as described above in FIGS. 1 to 6. The substrate 606 is also used as a separation material that separates the heater 608 from the fluid flowing in the fluid channels 616 in case the base dielectric layer 604 breaks. While not shown in the drawing, a protection housing may be provided to enclose and protect at least the heater 608.

The present disclosure is merely exemplary in nature and, thus, variations that do not depart from the gist of the disclosure are intended to be within the scope of the present disclosure. For example, although a geometric configuration of a heating device having a channel formed therethrough has been illustrated and described herein, it should be understood that the various constructions according to the present disclosure may also be employed with a flat heating device, among other geometries. Accordingly, the tubular configurations disclosed herein should not be construed as limiting the scope of the present disclosure. Such variations are not to be regarded as a departure from the spirit and scope of the present disclosure.

What is claimed is:

1. An electrical heating device for medical equipment, the electrical heating device comprising:
   a conducting body that is electrically conductive and that forms a channel therethrough for fluid travel;
   a base dielectric layer disposed on the conducting body;
   a heater surrounding the base dielectric layer and the conducting body;
   a top dielectric layer disposed on the heater; and
   a protection housing that is preformed and that defines a cavity to receive the top dielectric layer and the heater in the cavity, the base dielectric layer and the top dielectric layer jointly enclosing the heater such that no portion of the heater is exposed from the base dielectric layer and the top dielectric layer, wherein the protection housing defines side pieces that are in direct contact with the conducting body.

2. The electrical heating device according to claim 1, wherein the heater being formed by a layering process.

3. The electrical heating device according to claim 1, wherein the protection housing is electrically conductive.

4. The electrical heating device according to claim 3, wherein the protection housing cooperates with the conducting body to encapsulate the base dielectric layer, the heater, and the top dielectric layer.

5. The electrical heating device according to claim 4, further comprising an electrically and thermally insulating compound disposed around the top dielectric layer, the compound being encapsulated by the protection housing and the conducting body.

6. An electrical heating device comprising:
   a body;
   a base layer dielectric disposed proximate the body;
   a heater disposed proximate the base layer dielectric;
   a top dielectric layer disposed proximate the heater; and
   a protection housing that is preformed and that defines a cavity to receive the heater, the top dielectric layer and the base layer dielectric,
   wherein the base layer dielectric and the top dielectric layer cooperate to encapsulate the heater such that no portion of the heater is exposed from the base layer dielectric and the top dielectric layer, the base layer dielectric and the top dielectric layer being disposed within the cavity of the protection housing, and the protection housing defining side pieces that are in direct contact with the body.

7. The electrical heating device according to claim 6, wherein at least one of the base dielectric layer, the top dielectric layer, and the heater are formed by a layering process.

8. The electrical heating device according to claim 6, further comprising an electrically and thermally insulating compound disposed within the protection housing and surrounding the heater, the top dielectric layer, and the base layer dielectric.

9. The electrical heating device according to claim 6, wherein the body forms a channel therethrough for fluid travel.

10. The electrical heating device according to claim 6, wherein the body is flat.

11. The electrical heating device according to claim 6, further comprising a plurality of channels formed through the body proximate the insulating material.

12. An electrical heating device for medical equipment, the electrical heating device comprising:
    a conducting body that is electrically conductive and that forms a channel therethrough for fluid travel;
    a tubular outer portion that is preformed and that that surrounds the conducting body;
    side pieces that connect opposing ends of the tubular outer portion and opposing ends of the conducting body to define an annular cavity between the conducting body, the tubular outer portion and the side pieces;
    a heater disposed in the cavity;
    a base dielectric layer and a top dielectric layer that sandwich the heater therebetween and that completely enclose the heater therein such that no part of the heater is exposed from the base dielectric layer and the top dielectric layer.

13. The electrical heating device according to claim 12, further comprising an electrically and thermally insulating compound disposed in the annular cavity and surrounding the top dielectric layer.

14. The electrical heating device according to claim 13, wherein the electrically and thermally insulating compound is in direct contact with the side pieces and the top dielectric layer.

15. The electrical heating device according to claim 12, wherein the side pieces are separate components from the tubular outer portion.

16. The electrical heating device according to claim 12, wherein the side pieces are welded to the tubular outer portion.

17. The electrical heating device according to claim 12, wherein the side pieces are fixed to the conducting body.

18. The electrically heating device according to claim 12, wherein the side pieces are welded to the conducting body.

19. The electrical heating device according to claim 12, wherein the tubular outer portion and the side pieces are made of an electrically conducting material.

20. The electrical heating device according to claim 12, wherein the heater is formed by a layering process.

* * * * *